United States Patent [19]
Hardy et al.

[11] Patent Number: 5,326,555
[45] Date of Patent: Jul. 5, 1994

[54] CLEAR HAIR SPRAY COMPOSITION CAPABLE OF FORMING LOW TACK FILMS WHICH DRY RAPIDLY

[75] Inventors: Eugene E. Hardy, Saddle Brook; Edward W. Walls, Jr., Cranford, both of N.J.

[73] Assignee: ISP Investments Inc., Wilmington, Del.

[21] Appl. No.: 34,999

[22] Filed: Mar. 22, 1993

[51] Int. Cl.$^5$ .................... A61K 7/11; A61K 31/765; C08L 33/02

[52] U.S. Cl. ........................................ 424/71; 424/47; 424/78.02; 424/78.21; 424/DIG. 1; 424/DIG. 2; 525/207

[58] Field of Search ............... 424/47, 70, 71, DIG. 1, 424/DIG. 2, 78.02, 78.21; 525/207, 221; 526/272, 318.25

[56] References Cited

U.S. PATENT DOCUMENTS 5,032,391 7/1991 Helioff et al. .......................... 424/70
5,164,177 11/1992 Bhatt et al. ............................ 424/47

*Primary Examiner*—Edward Webman
*Attorney, Agent, or Firm*—Walter Katz; Marilyn J. Maue; Joshua J. Ward

[57] ABSTRACT

A clear hair spray composition exhibiting low drying times and low tack during use consisting essentially of, by weight of the composition,
(a) 0–10% of a fixative resin that is a linear homopolymer or random copolymer including a monomer selected from the group consisting of a vinyl monomer and an acrylate monomer,
(b) 0.01–10% of a hydrolyzed crosslinked maleic anhydride-$C_1$–$C_5$ alkyl vinyl ether copolymer,
(c) 10–99.99% water, and
(d) 0–80% alcohol.

9 Claims, No Drawings

CLEAR HAIR SPRAY COMPOSITION CAPABLE OF FORMING LOW TACK FILMS WHICH DRY RAPIDLY

BACKGROUND OF THE INVENTION

1. Field of the Invention

This invention relates to hair spray compositions, and, more particularly, to non-aerosol or aerosol hair spray compositions which provide films having low drying times and low tack during use.

2. Description of the Prior Art

Almost all commercial hair spray compositions contain ethanol as a solvent for the film-forming hair fixative resin. However, ethanol is disfavored because it is a volatile organic compound (VOC) which can pollute the air; also it can give beauticians upper respiratory infections and irritations of the nose and skin. Accordingly, it is desired to provide a hair spray product which has a substantially reduced amount of alcohol therein, or is alcohol-free, i.e., it is a water-based formulation, and which can perform as effectively as an ethanol-based product. Most particularly, what is desired is a clear, non-foaming aqueous-based composition suitable for use in both non-aerosol and aerosol delivery systems which provide tack-fee films which dry rapidly.

SUMMARY OF THE INVENTION

A clear hair spray composition exhibiting low drying times and low tack during use consisting essentially of, by weight of the composition, (a) 0–10% of a fixative resin that is a linear homopolymer or random copolymer including a monomer selected from the group consisting of a vinyl monomer and an acrylate monomer, (b) 0.01–10% of a hydrolyzed crosslinked maleic anhydride-$C_1$–$C_5$ alkyl vinyl ether copolymer, (c) 10–99.99% water, and (d) 0–80% alcohol.

DETAILED DESCRIPTION OF THE INVENTION

(a) Fixative Resin

If present, polymers that are soluble or dispersible in the aqueous phase may be used. When an optional co-solvent such as ethanol is present in the composition, the polymer should be soluble or dispersible in the combined solvent system. Solubility or dispersibility is determined at ambient conditions (e.g. a temperature of about 25° C. and atmospheric pressure).

The polymers or resins useful in the compositions of the present invention are homopolymers or copolymers that can be rendered dispersible or soluble in aqueous or hydroalcoholic solvent mixtures. To achieve the full advantage of the present invention, the fixative resin should be a synthetic, linear, homopolymer or random copolymer including at least one, and preferably two or more, vinyl or acrylate monomers of the following group:

alkyl vinyl ethers

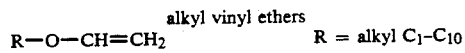

R = alkyl $C_1$–$C_{10}$

Alkyl Acrylates

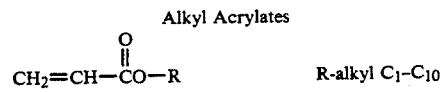

R-alkyl $C_1$–$C_{10}$

Vinyl esters

R = alkyl $C_1$–$C_{10}$

N-vinyl lactams

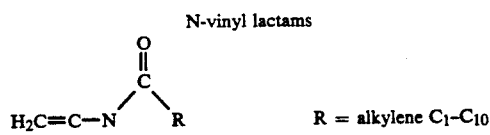

R = alkylene $C_1$–$C_{10}$

Alkyl acrylamides

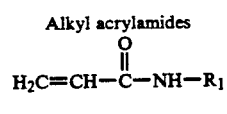

$R_1$-alkylene $C_1$–$C_{10}$

Half vinyl esters/half amides

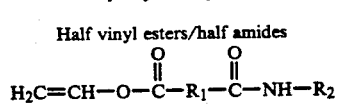

$R_1$ = alkylene $C_1$–$C_{10}$ $R_1$ = alkyl $C_1$–$C_{10}$

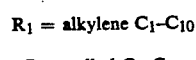

R = alkyl $C_1$–$C_{10}$

Acrylic acid

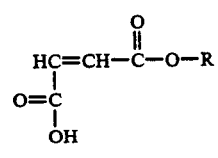

Crotonic acid

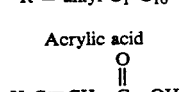

Methacrylic acid

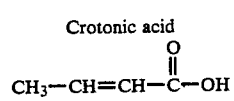

If the fixative resin in a copolymer, the copolymer preferably includes from about 5% to about 13% by weight of a polymerizable carboxylic acid such as acrylic acid, crotonic acid, methacrylic acid or a combination thereof. In addition, in most copolymers, the ratio of water soluble monomers, such as N-vinyl lactams and acrylamides, in the polymer is maintained relatively low to reduce the tackiness and moisture sensitivity of the resin. For this reason and depending on the polymer, usually 5 to 15 acid units are required to render the polymer soluble in polar solvents, such as water, alcohols, ketones, glycol ethers, liquified dimethyl ether, and mixtures through neutralization with a suitable base.

Examples of preferred copolymers are the mono ethyl, isopropyl or n-butyl esters of poly(methyl vinyl ether/maleic acid); poly(vinyl pyrrolidone/ethyl methacrylate/methacrylic acid), poly(ethyl acrylate/acrylic acid/N-t-butyl acrylamide), and poly(vinyl acetate/crotonic acid). The compositions of the present invention preferably include from about 0.01% to about 10% resin to provide the best esthetics and spray delivery.

Other suitable classes of polymers include anionic, nonionic, amphoteric and cationic polymers. Specific polymers include polyvinylpyrrolidone (PVP), copolymers of (PVP) and methylmethacrylate, copolymers of PVP and vinyl acetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer and octylacrylamide/acrylate/butylaminoethyl methacrylate copolymers, and mixtures.

With certain of the acidic polymers, it may be necessary to neutralize some acidic groups to promote solubility/dispersibility, e.g., PVA/crotonic acid. Neutralization and increased solubilization are accomplished with one or more inorganic bases such as sodium hydroxide, potassium hydroxide, ammonium hydroxide and/or ammonium carbonate. Among stable organic bases are the water soluble bases such as monoethanolamine (MEA), diethanolamine (DEA), triethanolamine (TEA), 2-amino-2-methyl-1-propanol (AMP), monoamino glycols, and the like, which help solubilize the polymer in water solutions. The level of neutralization required for solubilization varies for each polymer. All of the above-described acidic polymers become soluble in water and hydroalcoholic solutions at 100% neutralization, and all described levels of water/alcohol/propellant solutions. The pH of these solutions usually ranges from about 9 to about 12. The lowest neutralization level needed to render the polymer water soluble or dispersible depends on the kind of polymer, and the amount of alcohol, water, and propellant. For instance, for poly(methyl vinyl ether/maleic acid) in water the lowest neutralization level is about 40% with sodium hydroxide and AMP; for poly(ethyl acrylate/acrylic acid/N-t-butyl acrylamide) the lowest neutralization level is about 75% with AMP and 65% with sodium hydroxide. At these neutralization levels, the pH of the solutions ranges from about 5 to about 7. A substantially neutral pH is preferred, however, the pH of the compositions of the present invention can vary from about 4 to about 13.

(b) Crosslinked polymer

As a feature of this invention, the hair spray composition includes about 0.01–10%, preferably about 0.08–0.2%, by weight, of a crosslinked maleic anhydride-$C_1$-$C_5$ alkyl vinyl ether copolymer, such as described in U.S. Pat. No. 5,032,391, the entire contents of which are incorporated by reference herein. These crosslinked copolymers are prepared by polymerizing maleic anhydride, a $C_1$-$C_5$ alkyl vinyl ether and a crosslinking agent in the presence of a suitable free radical initiator.

Different solvents may be used for the polymerization, including benzene, toluene, xylene, acetone, methyl ethyl ketone and methylene chloride; however, it is preferred to use a mixture of a carboxylic acid ester and a saturated cycloaliphatic hydrocarbon. A particularly preferred solvent system is a mixture of ethyl acetate and cyclohexane, preferably in the weight ratio of about 35 to 55% ethyl acetate to about 45 to 65% cyclohexane.

In this solvent system, the crosslinked copolymer product is provided in pumpable slurry form, from which dry, fine, white powders can be obtained easily. The copolymer powders can be readily hydrolyzed to clear gels of high viscosities with good stability and excellent salt tolerance.

The amount of crosslinking agent used in polymerization generally varies from about 1 to about 5 mole percent based on the monovinyl alkyl ether. Examples of suitable crosslinking agents include diunsaturated compounds such as the divinyl ethers of an aliphatic diol, e.g. the divinyl ethers of 1,2-ethanediol; 1,3-propanediol; 1,4-butanediol, 1,5-pentanediol; 1,6-hexanediol; 1,7-heptanediol; 1,8-octanediol; 1,9-nonanediol; 1,10-decanediol; 1,11-undecanediol; and 1,12-dodecanediol, as well as the divinyl ethers of diethylene glycol, triethylene glycol, tetraethylene glycol, pentaethylene glycol; hexaethylene glycol, heptaethylene glycol, octaethylene glycol, nonaethylene glycol, decaethylene glycol and further polyalkylene glycols up to a molecular weight of about 5900. Other suitable crosslinking agents include 1,7-octadiene, 1,9-decadiene, divinylbenzene, N,N'-bis-methylene acrylamide, acrylates such as polyethylene glycol diacrylate, trimethylolpropane triacrylate, propylene glycol diacrylate, polyhydric alcohols esterified once or twice with acrylic acid triallylamine, tetraallylehylenediamine, diallyl phthalate, and the like.

The polymerization is carried out conveniently by preparing the mixed solvent solution of the monomers and adding a catalytic amount (generally from 0.001 to 1.0%) of an organic free radical-generating initiator. The resulting solution then is mixed thoroughly and heated sufficiently so that the polymerization reaction takes place. At the completion of the polymerization reaction, the precipitated interpolymer is isolated by any suitable means such as by filtration or distillation of solvent, then washed with fresh solvent and vacuum dried.

Suitable organic free radical-generating initiators includes azobisisobutyronitrile, benzoyl peroxide, lauroyl peroxide, caprylyl peroxide, acetyl peroxide, acetyl benzoyl peroxide, di-tert-butyl peroxide, t-butyl peroxypivalate, azobis(2,4-dimethylvaleronitrile) and the like. Mixtures of such catalysts are also suitable in the process of making the interpolymers of the invention.

The polymerization is carried out at a temperature within the range of from 50° to 100° C., particularly about 60°–80° C.

After obtaining the dry powder copolymer, the anhydride groups thereof are hydrolyzed in aqueous solution at a suitable temperature, e.g. about 60°–75° C. The resultant pH of the clear hydrolyzed copolymer is about 4–6, preferably 4.4–4.6.

(c) Water

Suitably, about 10–99.99% by weight of the composition is water, preferably about 11.8–41.92%.

(d) Alcohol

The composition may include up to 80% by weight of alcohol, preferably about 55–80%. The optional alcohol employed in the composition is an aliphatic straight or branched chain monohydric alcohol having 2 to 4 carbon atoms. Isopropanol and especially ethanol are preferred.

The resultant hair spray composition of the invention is a clear, non-foaming, aqueous-based formulation which can be sprayed onto the hair of the user using a non-aerosol (pump actuated) or an aerosol delivery system with a propellant gas.

The propellant gas included in the aerosol compositions of the present invention can be any liquefiable gas conventionally used for aerosol containers. Examples of materials that are suitable for use as propellants are trichlorofluoromethane, dichlorodifluoromethane, dichlorotetrafluoroethane, monochlorodifluoromethane, trichlortrifluoroethane, dimethyl ether, propane, n-butane and isobutane, used singly or admixed. Water-soluble gases such as dimethyl ether, carbon dioxide, and/or nitrous oxide also can be used to obtain aerosols having reduced flammability.

Water-immiscible, liquified, hydrocarbon and halogenated hydrocarbon gases such as propane, butane and chlorofluorocarbons can be used advantageously to deliver the contents of the aerosol container without the dramatic pressure drops associated with other immiscible gases. Here there is no concern for the head space to be left inside the aerosol container, because the liquified gas will sit on top of the aqueous formulation and the pressure inside the container is always the vapor pressure of saturated hydrocarbon vapor.

Other insoluble, compressed gases such as nitrogen, helium and fully-fluorinated oxetanes and oxepanes also are useful to deliver the compositions from aerosol containers. Other means of delivery of the above-described aqueous styling aid compositions include, pump sprayers, all forms of bag-in-can devices, in situ carbon dioxide ($CO_2$) generator systems, compressors, and the like.

The invention will now be described with reference to the following examples.

EXAMPLE 1

Preparation of Crosslinked Copolymer

A reactor was precharged with a 50:50 weight mixture of ethyl acetate and cyclohexane as a cosolvent composition, and 1,7-octadiene as a crosslinking agent. The reactor was then purged with nitrogen, heated to 58° C., and charged with initiator (Lupersol-11 which is t-butyl peroxypivalate) at a 0.15 to 2% by weight level based on maleic anhydride (MA). Then molten maleic anhydride and methyl vinyl ether (MVE) were fed separately (or through a common inlet) into the reactor over a 2 to 3 hour period. The reactants were held at that temperature for an additional 1 to 3 hours, then cooled, vented and discharged. The resulting slurry, in which the copolymer product was present at an 18 to 25% solids level, was filtered and dried. Fine white powders of the desired crosslinked copolymer were obtained.

EXAMPLE 2

Preparation of Hydrolyzed Crosslinked Copolymer 1.47 g. of the crosslinked copolymer prepared above in 98.53 g. of water were heated at 75° C. to form a clear gel base having a viscosity of 150,000 cps, and it was stable at that value at room temperature for an extended period of time.

EXAMPLE 3

Preparation of Hair Spray Composition of Invention 13.6 g. of the hydrolyzed crosslinked copolymer gel base prepared above, 79.87 g. of ethanol, 12 g. of Gantrez® V-225 (50% solids in ethanol) (ISP) and 0.53 g. of 2-amino-2-methyl-1-propanol (AMP-95) were mixed to form a clear, non-foaming solution.

EXAMPLE 4

Properties of Composition of Example 30 in Use as a Hair Styling Aid

The hair spray composition of Example 3 with varying amounts of hydrolyzed crosslinked copolymer therein were evaluated for its performance on hair with respect to (a) the dry time, i.e. the total time required to completely dry the hair; and (b) the tack-free time, i.e. the time required to make the hair "feel" dry. These time periods are measured from application of the composition to the hair to achievement of the desired hair condition. The results of these tests are shown in the Table below.

TABLE

| Amount of Hydrolyzed Crosslinked Copolymer (%) in Hair Spray Composition | (a) Drying Time (Sec.) | (b) Tack-Free Time (Sec.) |
| --- | --- | --- |
| None (Control) | 80.0 | 51.0 |
| 0.08 | 69.7 | 40.7 |
| 0.14 | 65.0 | 34.3 |
| 0.20 | 59.3 | 33.0 |

These results demonstrate that the presence of the hydrolyzed crosslinked copolymer in the composition of the invention substantially reduces the total drying time and the tack-free time of the hair spray as compared to compositions (control) without this component.

While the invention has been described with particular reference to certain embodiments thereof, it will be understood that changes and modifications may be made which are within the skill of the art. Accordingly, it is intended to be bound only by the following claims, in which:

We claim:

1. A clear hair spray composition exhibiting reduced drying times and reduced tack during use as compared to compositions without component (b) below being present, consisting essentially of, by weight of the composition,
    (a) about 2–9% of a fixative resin that is a linear homopolymer or random copolymer including a monomer selected from the group consisting of a vinyl monomer and an acrylate monomer,
    (b) about 0.08–0.35% of a hydrolyzed crosslinked maleic anhydride-$C_1$–$C_5$ alkyl vinyl ether copolymer,
    (c) about 11.8–41.92% water, and
    (d) about 55–80% alcohol having 2–4 carbons.

2. A composition according to claim 1 wherein (b) includes about 1–5 mole % based on the alkyl vinyl ether of a difunctional crosslinking agent.

3. A hair spray product comprising the composition of claim 1 and a non-aerosol delivery system.

4. A hair spray product comprising the composition of claim 1 and an aerosol delivery system which includes a propellant.

5. A composition according to claim 1 in which (a) includes a vinyl monomer.

6. A composition according to claim 1 in which (a) includes an acrylate monomer.

7. A composition according to claim 1 wherein (a) is a homopolymer or random copolymer selected from the group consisting of alkyl vinyl ethers, alkyl acrylates, vinyl alkyl esters, N-vinyl lactams, alkyl acrylamides, half vinyl esters/half amides, half esters of maleic anhydride, acrylic acid, crotonic acid, methacrylic acid, and mixtures thereof.

8. A composition according to claim 1 wherein the fixative resin is a copolymer containing at least two monomers selected from the group consisting of vinyl and acrylic monomers.

9. A composition according to claim 1 which is non-foaming.

* * * * *